United States Patent
Shoham et al.

(10) Patent No.: US 8,207,499 B2
(45) Date of Patent: Jun. 26, 2012

(54) VARIABLE RATE SCANNING IN AN ELECTRON MICROSCOPE

(75) Inventors: Amir Shoham, Haifa (IL); Benzion Sender, Modiin (IL); Alon Litman, Nes Ziona (IL)

(73) Assignee: Applied Materials Israel, Ltd., Rehovot (IL)

( * ) Notice: Subject to any disclaimer, the term of this patent is extended or adjusted under 35 U.S.C. 154(b) by 625 days.

(21) Appl. No.: 12/237,364

(22) Filed: Sep. 24, 2008

(65) Prior Publication Data

US 2010/0072365 A1     Mar. 25, 2010

(51) Int. Cl.
*H01J 37/26* (2006.01)

(52) U.S. Cl. ......... 250/307; 250/306; 250/310; 250/311

(58) Field of Classification Search .............. 250/306, 250/307, 309, 310, 311; 430/296
See application file for complete search history.

(56) References Cited

U.S. PATENT DOCUMENTS

| | | | |
|---|---|---|---|
| 3,703,637 A * | 11/1972 | Dugan | 850/63 |
| 4,611,119 A | 9/1986 | Fazekas et al. | |
| 4,922,106 A | 5/1990 | Berrian et al. | |
| 7,982,186 B2 | 7/2011 | Kanai | |
| 8,063,363 B2 | 11/2011 | Yeh | |
| 2004/0041095 A1 * | 3/2004 | Nasser-Ghodsi et al. | 250/310 |
| 2004/0183013 A1 * | 9/2004 | Nakasuji et al. | 250/310 |
| 2006/0097200 A1 * | 5/2006 | Nakasuji et al. | 250/493.1 |
| 2007/0176101 A1 | 8/2007 | Proksch et al. | |
| 2007/0272857 A1 | 11/2007 | Hasegawa et al. | |

OTHER PUBLICATIONS

Shimomura et al. "Demonstration of defect free EUV mask for 22nm NAND flash contact layer using electron beam inspection system", Proc. of SPIE vol. 7969, pp. 79691B-1 to 79691B-8, Feb. 28, 2011.
Applied Materials Israel, Ltd.; CN Application No. 200910170555. X; First Office Action mailed Oct. 10, 2011; 11 pages.

* cited by examiner

*Primary Examiner* — David A Vanore
*Assistant Examiner* — Nicole Ippolito
(74) *Attorney, Agent, or Firm* — Tarek N. Fahmi, APC (57) ABSTRACT

A method for imaging a surface, including scanning a first region of the surface with a primary charged particle beam at a first scan rate so as to generate a first secondary charged particle beam from the first region, and scanning a second region of the surface with the primary charged particle beam at a second scan rate faster than the first scan rate so as to generate a second secondary charged particle beam from the second region. The method also includes receiving the first secondary charged particle beam and the second secondary charged particle beam at a detector configured to generate a signal in response to the beams, and forming an image of the first and the second regions in response to the signal.

12 Claims, 8 Drawing Sheets

VARIABLE RATE SCANNING IN AN ELECTRON MICROSCOPE

FIELD OF THE INVENTION

The present invention relates generally to imaging of a surface, and specifically to imaging of the surface by irradiation with a charged particle beam.

BACKGROUND

One of the standard methods for imaging a surface, particularly the surface of a semiconductor wafer, is to irradiate the surface with an electron beam in an electron microscope. Secondary electrons from the surface are collected, and may be used to form an image of the irradiated surface. Typically, in order to image the complete surface of the wafer, the electron beam is scanned across the surface, and the surface is moved orthogonally to the direction of the scanned beam.

In industrial settings it is useful to reduce the time taken to form the image. In order to do this, both the electron beam scan rate, and the movement of the surface, are typically set to be as fast as possible.

U.S. Pat. No. 4,922,106 to Berrian et al., whose disclosure is incorporated herein by reference, describes an ion beam scanning system. The system is stated to attain a selected beam current on a target object.

U.S. Patent Application 2007/0176101 to Proksch et al., whose disclosure is incorporated herein by reference, describes varying a scan rate in scanning probe instruments.

U.S. Patent Application 2007/0272857 to Hasegawa et al., whose disclosure is incorporated herein by reference, describes a scanning electron microscope which is stated to allow the user to examine conditions such as inspection speed intuitively.

SUMMARY OF THE INVENTION

In an embodiment of the present invention, a surface, typically the surface of a semiconductor wafer, is imaged in a scanning charged particle beam microscope. In order to image the surface, regions on the surface are initially classified as being of two or more different levels of interest. Herein there are assumed to be two types of region, a first type having a high interest level, and a second type having a low level of interest. The high interest regions are scanned at a first, low, scan rate, to produce a high resolution image, and the low interest regions are scanned at a second, faster, scan rate, to produce a low resolution image. Delineating the surface into regions that have high and low interest levels, and imaging the regions at different resolutions, allows the complete surface to be imaged, without sacrificing the resolution of high interest regions.

Typically, the charged particle beam is scanned along a one dimensional line, and the surface is moved orthogonally to the one dimension, so that the scan performed by the microscope is in the form of a sawtooth scan, along a column of the surface having a direction defined by the movement of the surface. In one embodiment, the high interest regions typically include sets of parallel lines, such as sets of conducting connector lines on the surface. The columns of the sawtooth scan may be aligned to be in the same direction as the direction of the sets of parallel lines, so that one column includes at least one high interest region and one or more low interest regions. Typically there are multiple high interest regions separated by or interleaving adjoining low interest regions. The one dimensional scan rate is set to be fast when sections of the low interest regions are imaged, and slow when sections of the high interest line are imaged.

In an alternative embodiment, the charged particle beam is scanned over a two-dimensional area. The scan is typically in the form of a raster scan over the area, and comprises an imaging period and a non-imaging period. The latter, in the case of the raster scan, corresponds to the vertical flyback period. The surface is moved relative to the area so that first regions of the surface are imaged during the imaging periods, and second regions of the surface, separating or interleaving the first regions, are not imaged at all. The first and second regions form a column having a direction defined by the movement of the surface relative to the area.

The first regions are typically set to be high interest regions, the second regions are typically set to be low interest regions. For surfaces that have high interest regions in the form of parallel lines, such as conductor lines, separated by low interest regions such as insulating regions, the surface may be oriented so that the movement is orthogonal to the parallel lines. Parameters of the two-dimensional scan, and the rate of movement of the surface, may be adjusted so that the conductor lines are imaged, and the insulating regions are not imaged at all.

Imaging only certain areas of the surface, while not imaging other areas, significantly decreases the time needed for efficiently imaging required regions of the complete surface.

The present invention will be more fully understood from the following detailed description of the embodiments thereof, taken together with the drawings, a brief description of which follows.

DETAILED DESCRIPTION

Figure 1:
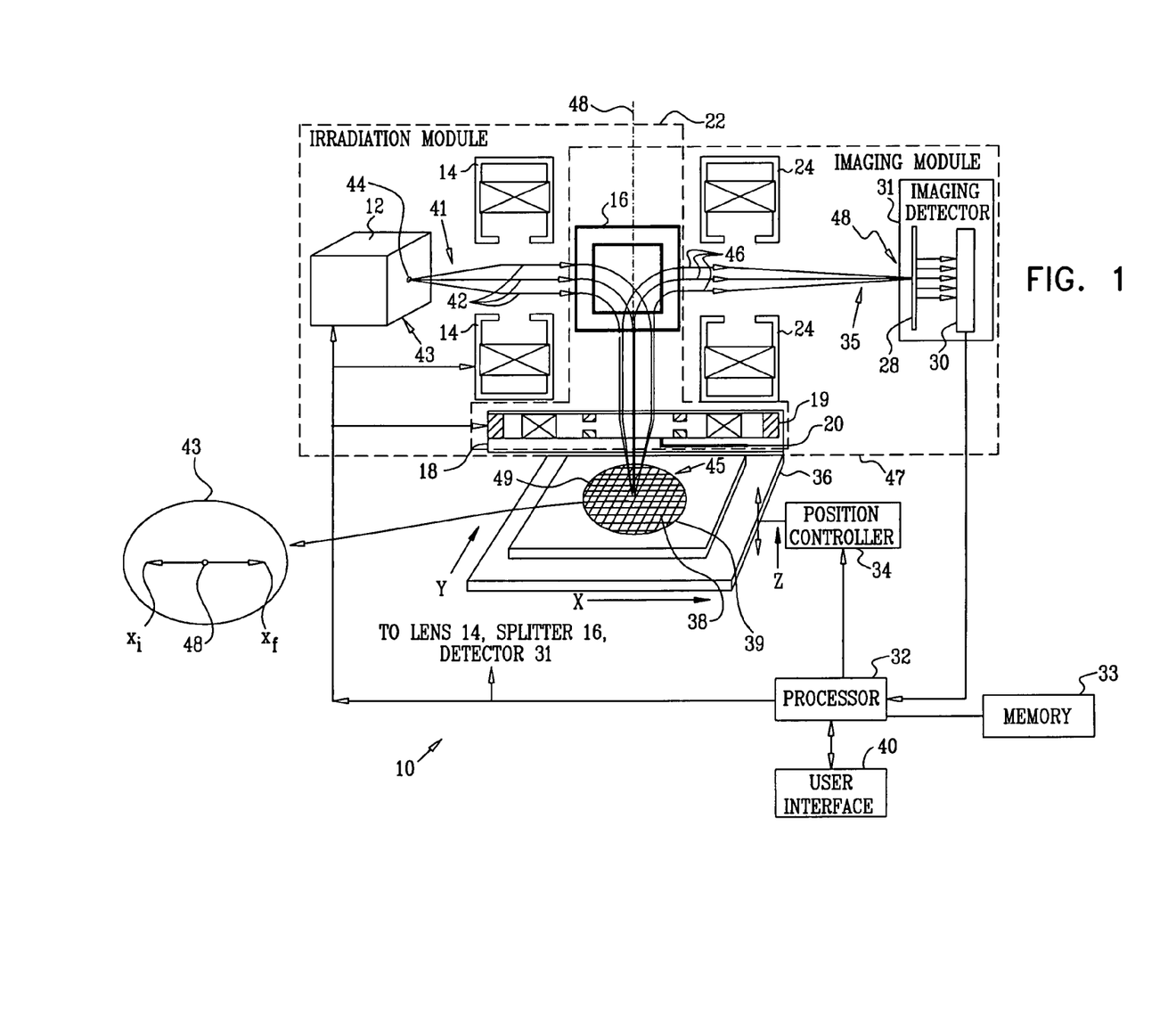
FIG. 1 is a schematic diagram of a charged particle beam focusing system, according to an embodiment of the present invention.

Reference is now made to FIG. 1, which is a schematic diagram of a charged particle beam focusing system 10, according to an embodiment of the present invention. System 10 includes a charged particle beam irradiation module 22, which, by way of example, is assumed to generate a single primary charged particle beam 41 from an aperture 44 of a charged particle gun 12. However, the scope of the present invention is not limited to generation of a single charged particle beam, so that module 22 may be configured to generate multiple beams.

Furthermore, the scope of the present invention is not limited to focusing a particular type of charged particle, and includes substantially all types of charged particles, including electrons and ions such as Gallium or other metallic ions. By way of example, the description hereinbelow assumes that the primary charged particle beam comprises electrons.

Module 22 comprises one or more illumination lenses 14, a beam splitter 16, and an objective lens 18, the lenses acting as focusing elements. Typically, the one or more lenses 14 and beam splitter 16 operate magnetically, although the lenses and/or the beam splitter may also incorporate other types of operation, such as electrostatic operation.

Figure 2:
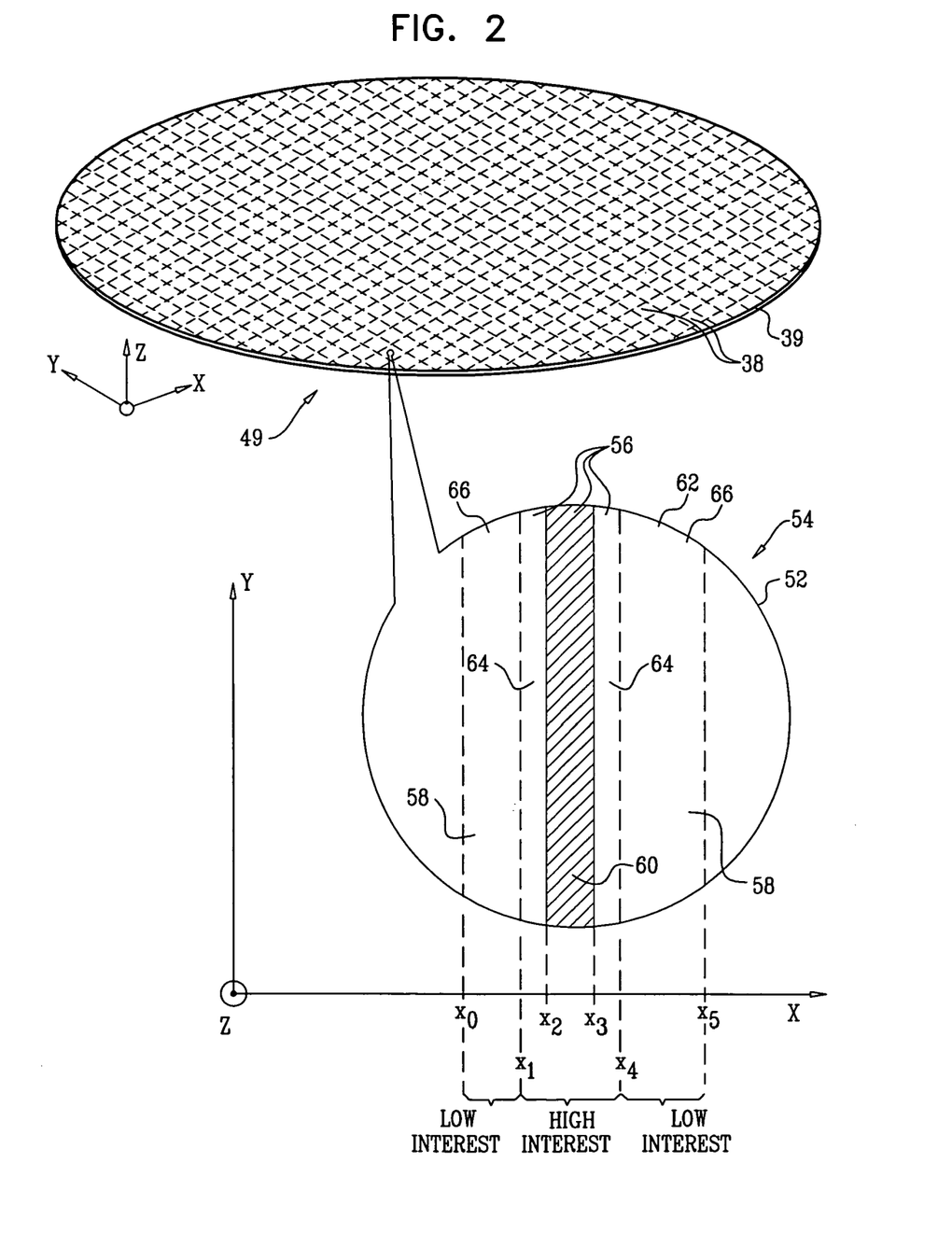
FIG. 2 is a schematic diagram of a surface of a wafer, according to an embodiment of the present invention.

Beam 41 follows an irradiation path 42 through module 22, and along an axis 48, to a surface 38 of a wafer 39, axis 48 typically being orthogonal to the surface. FIG. 2 illustrates the surface of wafer 39 in more detail. Wafer 39 is mounted on a movable stage 36, which is assumed to be able to translate the wafer parallel to three orthogonal axes x, y, and z, and the xy plane is assumed to be horizontal. The one or more lenses 14, beam splitter 16, and objective lens 18 form beam 41 into a focused image 45, hereinbelow also referred to as a spot 45, of aperture 44 on surface 38. As illustrated in FIG. 2, wafer 39 comprises a multiplicity of substantially similar dies 49, the dies having substantially congruent layouts. The dies are herein assumed to be rectangular dies having sides parallel to the x and y axes.

Spot 45 generates reflected, secondary, and/or back-scattered electrons as a secondary charged particle beam 35 of electrons, which passes through objective lens 18, and beam splitter 16. The secondary beam from spot 45 follows an imaging path 46, via an imaging lens 24 to an electron detector 28. Electron detector 28, typically a phosphor screen comprised of a scintillator crystal or a granulated scintillator powder, converts secondary beam 35 of electrons to optical radiation, which is imaged by an imager 30, such as a charge coupled detector (CCD) array. Detector 28 and imager 30 are typically combined as one unit, and act as an imaging detector 31 of the secondary beam, generating a signal indicative of the beam current. Alternatively, imaging detector 31 may comprise an avalanche photodiode array, which directly detects secondary beam 35 without conversion to light. Lenses 18 and 24, beam splitter 16, and imaging detector 31 comprise an imaging module 47 for system 10. The signal generated by imaging module 47 is transferred to a processor 32 coupled to a memory 33.

Processor 32 is coupled to gun 12, lenses 14, beam splitter 16, objective lens 18, imaging lens 24, and imaging detector 31, so as to control their operation and the focus of spot 45, and also so as to act as an overall controller of system 10.

Typically, processor 32 scans spot 45 in an x direction across dies 49, while the processor also moves the wafer in the y direction, by translating stage 36. As explained in more detail below, the spot travels in one x-direction, assumed to be the positive x-direction, at different substantially fixed scan rates during which surface 38 is imaged. Thus, the spot, as shows in an inset 43, scans from an initial x-value $x_i$ to a final x-value $x_f$, in an imaging phase. An intersection of axis 48 with surface 38 is approximately equidistant from $x_i$ and $x_f$. At the final x-value, the processor returns the spot to its initial x-value, at a high rate, during a horizontal flyback phase. During the flyback phase the processor sets the irradiation module to prevent the spot from striking surface 38, so that the horizontal flyback phase is a non-imaging phase.

Processor 32 thus translates spot 45 along a one-dimensional line, between the initial and final x-values. The combined linear x-scanning motion of the spot, together with the movement of the wafer in the y-direction, mean that surface 38 is scanned in a sawtooth manner. An effective width of the one-dimensional line translated by the spot corresponds to a dimension of a pixel, as is described in more detail below with respect to apparatus 410.

Hereinbelow it is assumed that processor 32 receives operating parameters from an operator of the system via a user interface 40, which enables the operator to adjust settings of the system components described above, as well as other components of system 10 described below. Processor 32 is also coupled to, and operates, a position controller 34. Under command of the processor, controller 34 is able to adjust stage 36 in a vertical direction.

The resolution of an image generated from the secondary beam current measurements is a function of the scan rate of spot 45. As the scan rate increases, the resolution of the image decreases. Conversely, as the scan rate decreases, the image resolution increases. In other words, the number of pixels into which a given region of the surface may be divided increases as the scan rate over the surface decreases.

FIG. 2 is a schematic diagram of surface 38 of wafer 39, according to an embodiment of the present invention. An inset 52 shows a section 54 of one die 49 in more detail, and a description is provided below, in reference to FIG. 3 and FIG. 4, for scanning a portion of section 54. Section 54 comprises different types of regions, each different type of region being assumed to generate a secondary beam 35 having a different beam current. There will typically be many such different regions, formed from one or more horizontal layers of wafer 39 having conducting, semiconducting, and/or insulating properties. Furthermore, each of the layers may be further differentiated. For example, conducting layers may be formed from different metals, or from the same type of metal with different dimensions, semiconducting layers may have different types of doping, and/or different dimensions, and insulating layers may be formed from different insulators or from the same insulators with different dimensions. In addition, any particular region of surface 38 may comprise one or more layers having different geometric arrangements. For example a first region may be formed from a first metal overlaying a doped semiconductor which in turn overlays a second metal, a second region may be formed from a metal overlaying an insulator, and a third region may be formed from a first metal separated by an insulator from a second metal, the three components being at the same horizontal level.

In an exemplary embodiment described hereinbelow, the regions into which section 54 is delineated are herein assumed to comprise a high interest region 56 and a low interest region 58. High interest region 56 is assumed to include a metallic line conductor 60 which overlays an untreated semiconducting substrate 62. The high interest region is also assumed to include edge portions 64 of the untreated substrate adjacent to, and on either side of, the conductor edges. Low interest region 58 is assumed to include sections 66 of the untreated substrate that are on either side of the high interest region. Typical properties of the line conductor that may cause it to be included in a high interest region may be the roughness of edges of the line conductor, changes in surface characteristics of the conductor, changes in width (between the edges) of the conductor, and/or changes in thickness of the conductor.

Wafer 39 is assumed to be aligned so that conductor 60 is parallel to the y-axis of apparatus 10, and so that a first edge of the conductor has a nominal x value $x_2$, and a second edge of the conductor has a nominal x value $x_3$. The wafer is scanned in a sawtooth fashion, as described above, and the sawtooth scan is assumed to have an initial x value $x_0$, and a final x value $x_5$.

High interest region 56 comprises a nominal area defined by the following expression:

$$\{(x,y) | x_1 < x < x_4\} \quad (1)$$

Conductor 60, which is nominally in a region defined by $\{(x,y) | x_2 < x < x_3\}$, is included in the high interest region.

Low interest region 58 comprises a nominal area defined by the following expression:

$$\{(x,y) | x_0 < x < x_1 \text{ or } x_4 < x < x_5\} \quad (2)$$

Expressions (1) and (2) delineate the sawtooth scan into low and high interest regions. As is described in more detail below with reference to flowchart 100, the two regions are scanned so that a high resolution image of high interest region 56 is formed, and so that a low-resolution image of low interest region 58 is formed.

Figure 3:
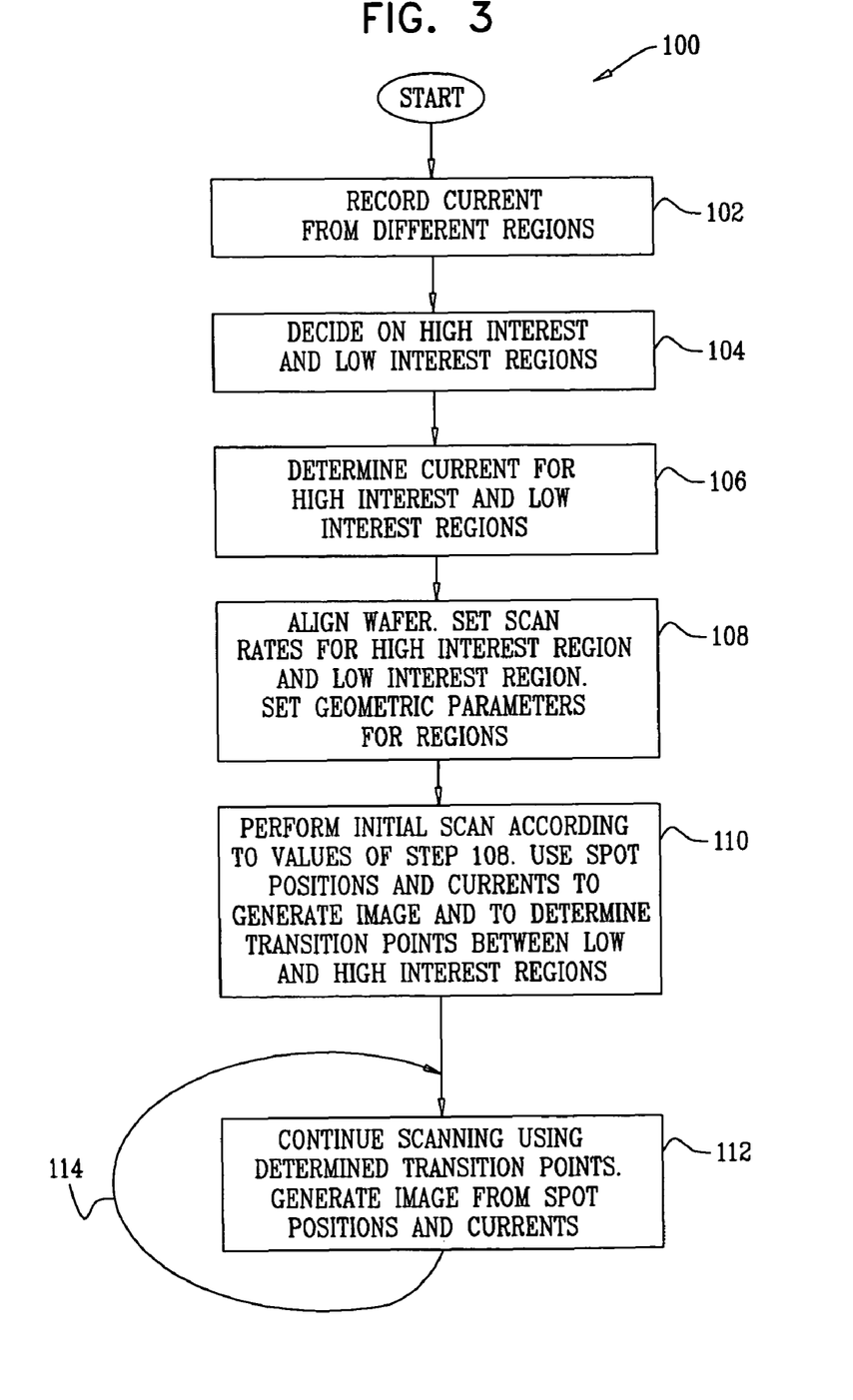
FIG. 3 is a flowchart of a scanning process for inspecting the surface of a wafer, according to an embodiment of the present invention.
Figure 4:
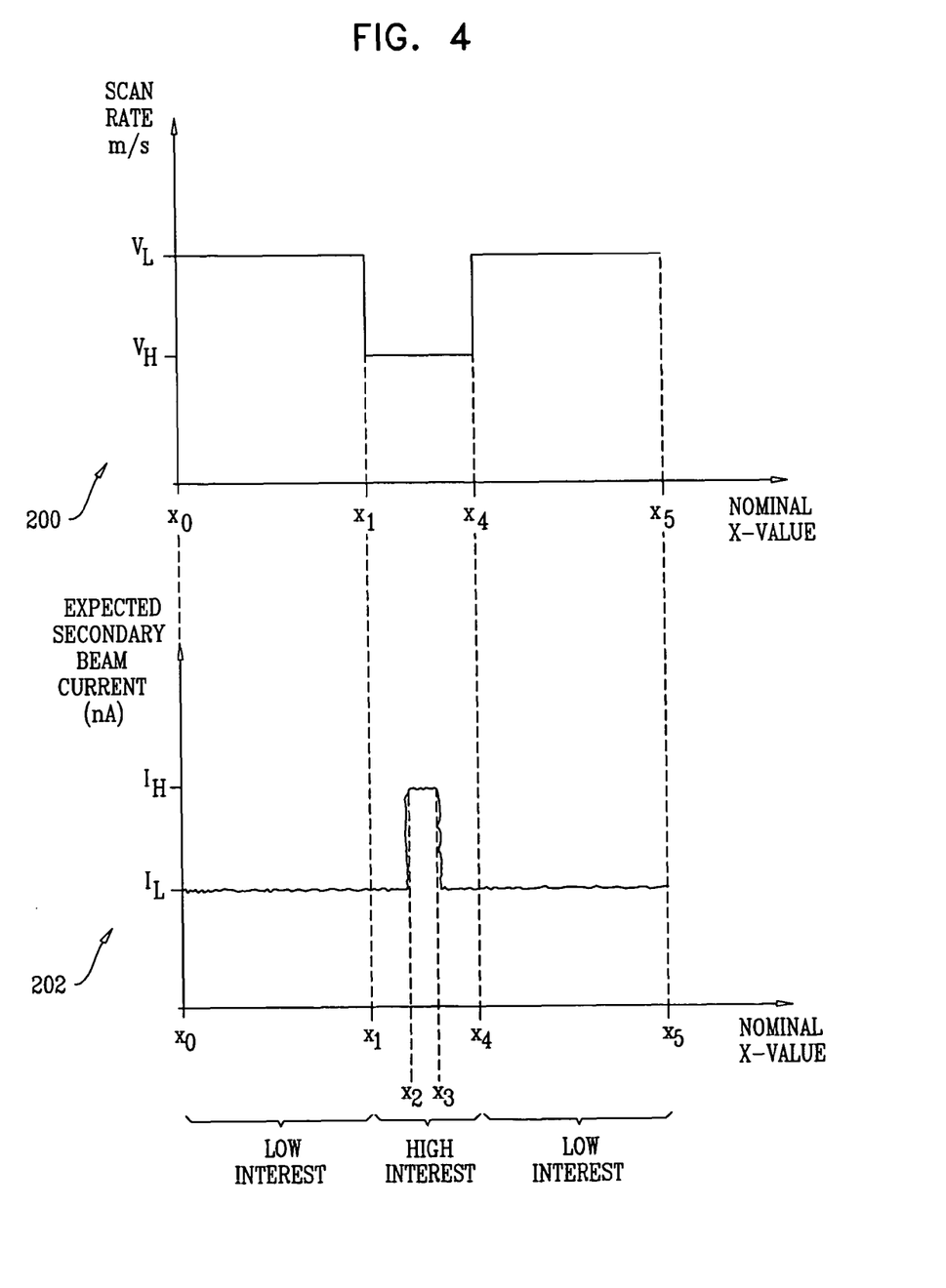
FIG. 4 shows graphs corresponding to the scanning process of FIG. 3, according to an embodiment of the present invention.

FIG. 3 is a flowchart 100 of a scanning process for inspecting the surface of a wafer, and FIG. 4 shows graphs corresponding to the scanning process, according to embodiments of the present invention. The scanning process is described with reference to section 54 of the die 49 described above.

In an initial step 102, an operator of system 10 configures processor 32 to determine currents of secondary beam 35 for different types of regions formed on surface 38, each type of region generating a characteristic value of the secondary beam current. The different currents may be determined by processor 32 making a preliminary scan of all or part of surface 38. Typically the preliminary scan is used to generate an image of the area scanned, and the image is presented to the operator on a screen comprised in user interface 40.

In a setup step 104, the operator decides regions of surface 38 which are high interest, and regions which are of low interest. In the example assumed herein, the operator selects metal line conductors to be included in high interest regions, and adds untreated regions of the substrate adjacent to the metal line conductors. The low interest regions are assumed to be untreated regions of the substrate adjacent to the high interest regions. The operator provides Cartesian coordinates of the two regions to the processor, typically by indicating with a pointing device on the image generated in initial step 102 positions or areas on surface 38, that are considered to be high interest, and those that are low interest. In the example considered here, the operator is assumed to define the high interest region according to expression (1), and the low interest region according to expression (2), and coordinates corresponding to these expressions are provided to the processor.

Typically, nominal values of $x_2$ and $x_3$ are available to the operator. As is apparent from expressions (1) and (2), the transitions, i.e., the boundaries, between the low interest and high interest regions, are given by x-values $x_1$ and $x_4$, where $x_1 < x_2$, and $x_4 > x_3$. Typically, the operator determines values of $x_1$ and $x_4$ based on $x_2$ and $x_3$.

By way of example, the areas of edge portions 64 are assumed to be equal, and to total to the area of conductor 60. In this case the following expressions hold:

$$(x_2 - x_1) = \frac{1}{2}(x_3 - x_2) \text{ giving } x_1 = \frac{3x_2 - x_3}{2} \quad (3)$$

-continued
$$(x_4 - x_3) = \frac{1}{2}(x_3 - x_2) \text{ giving } x_4 = \frac{3x_3 - x_2}{2} \quad (4)$$

In the following, it is assumed that the operator uses processor 32 to determine values of $x_1$ and $x_4$ according to expressions (3) and (4), thus delineating the high and low interest regions.

In a current-determining step 106 processor 32, with the assistance of the operator, determines secondary beam currents to be used in tracking the high interest and low interest regions. In the example used herein, the high-interest region comprises a metal conductor with edge portions of untreated substrate on either side of the conductor. The edge portions, defined by expressions (3) and (4) are defined in terms of the dimensions of the metal conductor, so that the secondary beam current generated by the metal conductor is selected by the operator to be a high interest region tracking current, also herein termed the high-interest-current, $I_H$.

The low interest region comprises only untreated substrate, so that the secondary beam current generated by the untreated substrate is selected to be a low interest region tracking current, also herein termed the low-interest-current, $I_L$.

Typically processor 32 has access to many values of currents generated by the metal conductor and the untreated substrate, from the currents measured in step 102. The processor may average appropriate values from these currents to determine an average current value for the high-interest-current, $I_H$, and for the low-interest-current, $I_L$. In some embodiments, such as if the operator is aware that the currents for a given region are abnormally distributed, the operator may override and/or assist the processor to set values of $I_H$ and $I_L$.

In an initialization step 108, the operator aligns the wafer so that conductor 60 is parallel to the y-axis, and so that a nominal x-value of spot 45 is $x_0$. The operator sets respective x-scan rates for the high interest region and the low interest region, as well as a y-scan rate at which the wafer is to be moved in the y-direction.

In some embodiments of the present invention, an x-scan rate for the low interest region, $v_L$, is determined by a bandwidth limit of the scanning electronics. In one such embodiment the bandwidth limited rate is approximately 450 m/s. A scan rate for the high interest region, $v_H$, depends on a desired pixel size and rate, and is typically within a range between approximately 1 m/s and approximately 50 m/s.

In addition, the operator sets the initial x parameters at which the different x-scan rates are to be applied, so that in the example considered here, the initial x parameters for $v_L$ are assumed to be given by expression (2), and the initial x parameters for $v_H$ are assumed to be given by expression (1). The settings of step 108 are illustrated in a graph 200 (FIG. 4). A graph 202 illustrates the corresponding expected current for the secondary beam.

Returning to FIG. 3, in a first scanning step 110, processor 32 begins scanning in the x direction from $x_0$ to $x_5$, using the initial parameters of step 108. Thus, in regions given by expression (1) the scan rate is slow, and in regions given by expression (2) the scan rate is fast. During the scan, the processor records the measured secondary beam current and the x and y positions at which the current is recorded. The currents are used to generate an image of the scanned region, so that a high resolution image is produced for positions where the scan rate is slow, and a low resolution image is produced where the scan rate is high.

In addition, processor 32 uses the measured currents to identify a first actual x-value, $_Ax_2$, where the secondary beam current transitions from a low interest region value to a high interest region value, and a second actual x-value, $_Ax_3$, for the opposite transition, i.e., from a high interest region value to a low interest region value. On reaching the end of the scan, i.e., at $x=x_5$, the processor returns spot 45 to $x_0$, in a horizontal flyback phase described above.

In a subsequent scanning step 112, the processor increments the value of y according to the y-scan rate and uses expressions (3) and (4), and the actual values $_Ax_2$ and $_Ax_3$ from step 110, to calculate updated actual values of $x_1$ and $x_4$, herein termed $_Ax_1$ and $_Ax_4$. The updated values $_Ax_1$ and $_Ax_4$ are respectively typically close to the nominal values $x_1$ and $x_4$. For the scan, processor 32 makes the transition from a high scan rate to the low scan rate, and vice versa, using updated values $_Ax_1$ and $_Ax_4$. As for step 110, the processor uses the received secondary beam currents and the positions of the spot generating the currents to generate an image of the scanned region.

The image formed comprises a high resolution image of the high interest region, where the scan rate is slow, and a low resolution image of the low interest region, where the scan rate is high. The ratio of the two resolutions is a function of the two scan rates, and is typically equal to the ratio of the two rates.

As shown by line 114, processor 32 iterates scanning step 112. The processor uses the actual x values of the current transitions (from a high level to a low level and vice versa) of one or more preceding scans to decide the transition points, i.e., the x-values, at which the scan rate of a present scan is to be changed. The processor thus uses x-values of previous scans as a feedback mechanism, so as to compensate for any change of x-values of the transition points from their nominal values.

Typically, the feedback mechanism incorporates a smoothing component. For example, a weighted average of the transition x-values of two or more previous scans may be used, the weighting being set according to how close in time a previous scan is to a present scan. However, processor 32 may use any other suitable smoothing method.

The process of flowchart 100 uses a sawtooth scan of all or part of a column on surface 38. Typically, the operator provides processor 32 with the y-values for the beginning and end of the column. In some embodiments, for example where conductor 60 extends along the whole of surface 38, the beginning and end y-values may correspond to the edge of wafer 39. In other embodiments, for example where conductor 60 only extends along a portion of the surface, the beginning and end y-values may be set to correspond to the ends of the conductor. Outside these y-values, the operator may configure processor 32 to scan the remainder of the column in a sawtooth manner, but with a single x-scan rate determined by the operator.

In general, it will be appreciated that the operator may define any region of surface 38, by providing processor 32 with appropriate Cartesian coordinates, to be scanned using the process of flowchart 100. Such a definition includes delineating areas of the region that are to be scanned at a high rate, so producing a low resolution image, and delineating areas that are to be scanned at a low rate, producing a high resolution image. In addition, any one column that is scanned need not comprise, as in the example described with reference to flowchart 100, one contiguous region of high interest with two low interest regions on either side. For example, one scanned column may comprise two or more thin metal conductors, parallel to the y-axis, separated by untreated substrate regions between the conductors. In this case an x-scan may be configured to scan the conductors as separate high interest regions, and the untreated substrate regions as separate low interest regions. An example of a scanned column comprising multiple regions or high interest separated by regions of low interest is described with respect to FIG. 5, below.

Figure 5:
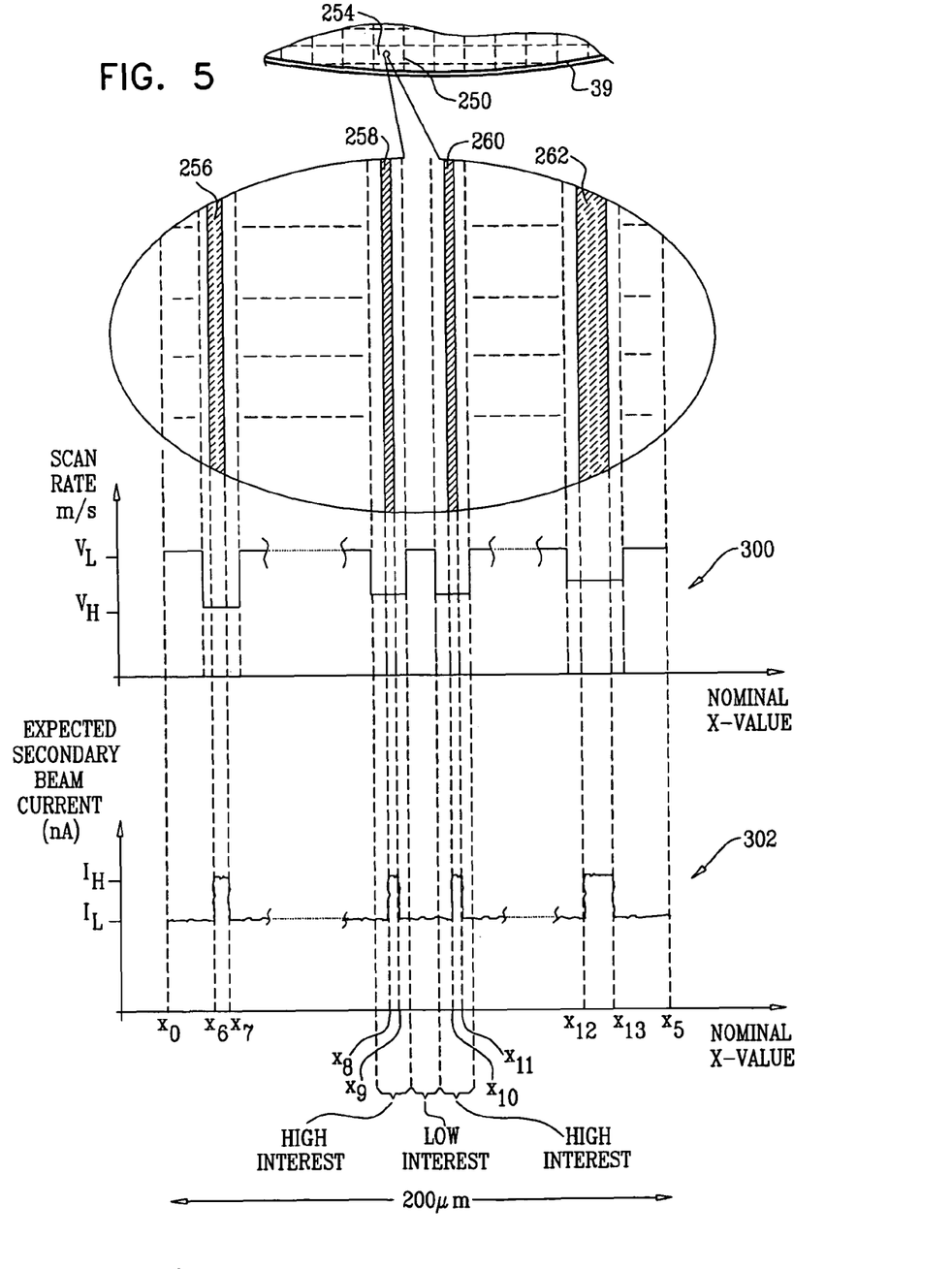
FIG. 5 is a schematic diagram of a section of a surface of a wafer, according to an alternative embodiment of the present invention.

FIG. 5 is a schematic diagram of a section 250 of surface 38 of wafer 39, according to an alternative embodiment of the present invention. Section 250 is typically larger than section 54 (FIG. 2), and is herein assumed to comprise multiple regions of high interest separated by regions of low interest.

In the following description, it is assumed by way of example that section 250 comprises multiple metal line conductors having a characteristic direction that is parallel to the y-direction, the conductors being separated by untreated substrate. The multiple conductors may be separated from each other by a substantially constant pitch, or by a variable pitch. In some embodiments the pitch is in a range between approximately 4 µm and approximately 10 µm. The multiple conductors may have equal widths, or may have different widths.

Section 250 comprises a region 254 that is irradiated by iteratively scanning spot 45 in the x-direction. Region 254 is assumed to have a width of 200 µm. Within region 254 FIG. 5 shows four exemplary conductors 256, 258, 260 and 262, although it will be understood that given the pitch values stated above, there may be between approximately 20 and approximately 50 conductors in the region. Conductors 258 and 260 are assumed to be adjacent to each other. In the following description, conductors 256, 258, 260, and 262 are assumed to have respective lower and upper x value bounds of $(x_6, x_7)$, $(x_8, x_9)$, $(x_{10}, x_{11})$ and $(x_{12}, x_{13})$.

The scanning process of flowchart 100 (FIG. 3), as described above, mutatis mutandis, is used to scan region 254. Referring back to the flowchart, initial step 102 is generally as described above. In setup step 104 the operator is assumed to decide that all metal conductors and areas adjacent to the conductors, covered by the scan, are to be included in high interest regions, and that untreated substrate regions between high interest regions are to be considered as low interest regions. The operator may delineate the high and low interest regions in a manner generally similar to that described above, applying expression similar to expressions (3) and (4) to the bounds of the metal conductors that are to be scanned. Alternatively the delineation may be by any other convenient means. For example, if a conductor such as conductor 262 is wider than other conductors being scanned, untreated regions of the substrate adjacent to the metal conductors may be delineated using the definition for the narrower conductors.

Current-determining step 106, to determine values of high-interest-current, $I_H$, and low-interest-current, $I_L$, and initialization step 108 are generally as described above. The settings of step 108 are illustrated in a graph 300. A graph 302 illustrates the corresponding expected current for the secondary beam.

In first scanning step 110, processor 32 begins scanning in the x direction, using the initial parameters of step 108. It will be understood that, for the multiple metal conductor lines example described herein, during one 200 µm scan of spot 45 there are a respective multiple number of periods during which the scan rate is low. These periods are separated by periods during which the scan rate is high. In scanning step 110 processor 32 finds multiple pairs of actual x-values, corresponding to the number of multiple conductors being scanned.

Subsequent scanning step 112 and its iterations are generally as described above, except that for the example described herein the processor determines multiple pairs of actual x values, corresponding to the transitions between high interest and low interest regions.

As for the example described above for one conductor, the image formed for the multiple conductor example comprises high resolution images of the high interest regions, where the scan rate is slow, and low resolution images of the low interest regions, where the scan rate is high.

The description above has assumed that two rates of scanning are applied to scans of a surface, generating images with two respective resolutions. However, it will be appreciated that by using more than two different scanning rates on different regions of the surface, principles of the present invention may be used to generate images of the different regions having resolutions respectively corresponding to the more than two different scanning rates.

Figure 6:
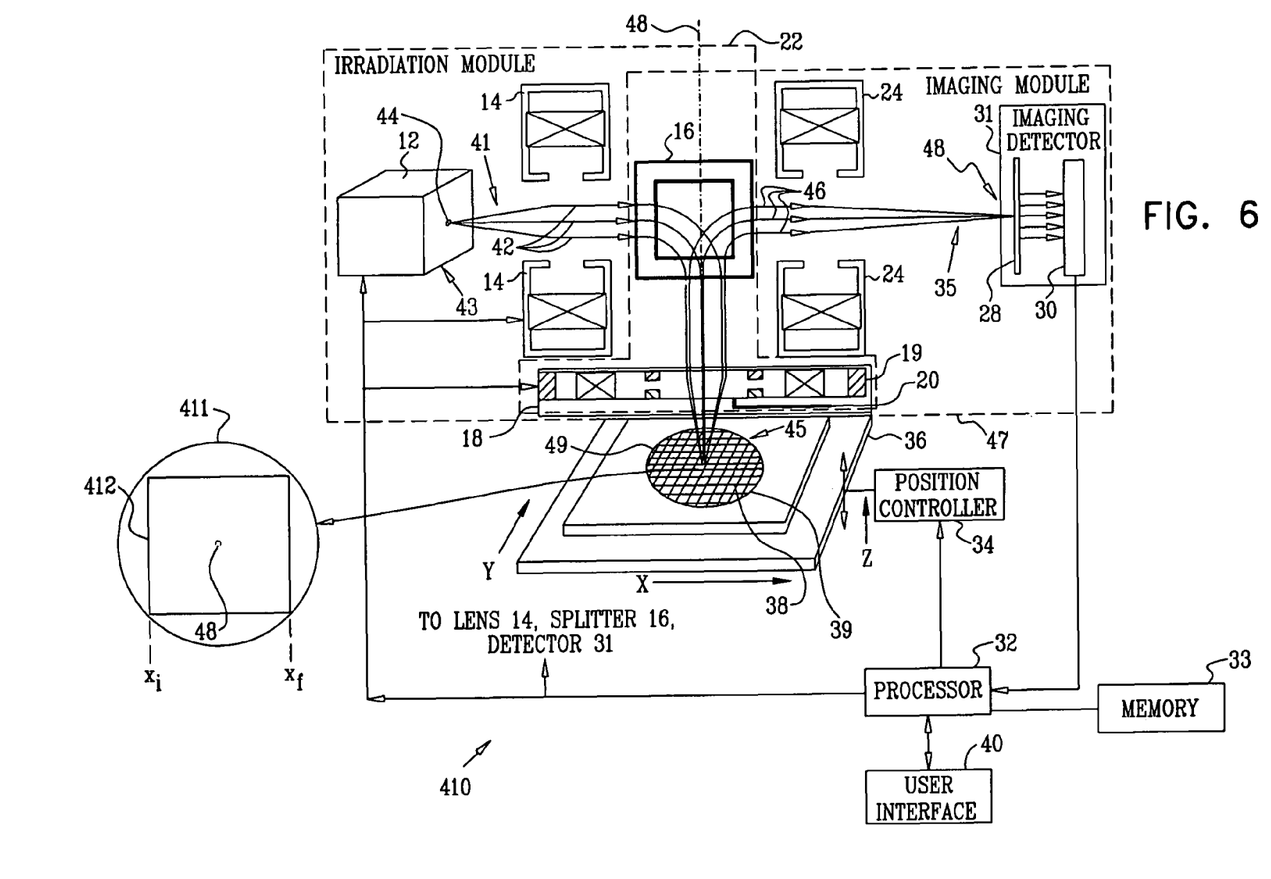
FIG. 6 is a schematic diagram of a charged particle beam focusing system, according to an alternative embodiment of the present invention.

FIG. 6 is a schematic diagram of a charged particle beam focusing system 410, according to an alternative embodiment of the present invention. Apart from the differences described below, the operation of apparatus 410 is generally similar to that of apparatus 10 (FIG. 1), and elements indicated by the same reference numerals in both apparatus 10 and 410 are generally similar in construction and in operation. Unlike apparatus 10, wherein processor 32 scans spot 45 linearly in one dimension, in apparatus 410 the processor scans the spot in two dimensions so that the spot traverses a rectangular area 412, also herein termed a window 412, as shown in an inset 411.

Figure 7:
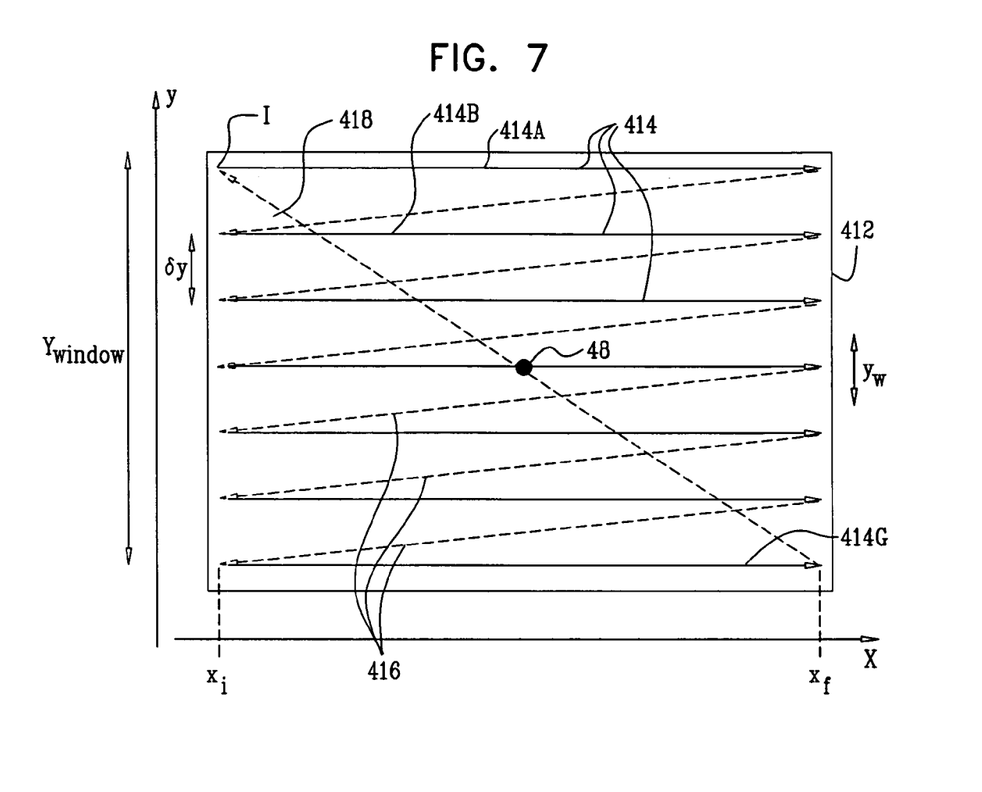
FIG. 7 is a schematic diagram of a path followed by a spot 45 in a window of the system of FIG. 6, according to an embodiment of the present invention.

FIG. 7 is a schematic diagram of a path followed by spot 45 in window 412, according to an embodiment of the present invention. Typically, the rectangular dimensions of window 412 are within limits defined by the ability of module 22 to maintain spot 45 in focus. By way of example, window 412 is assumed to be a rectangle, centered on the intersection of axis 48 with surface 38. In the figure, the y-axis and the x-axis are drawn to different scales.

Processor 32 scans spot 45 iteratively with a substantially constant overall period T. By way of example, the scan is assumed to begin with spot 45 in a position I, where I is a highest left-hand point in window 412. Also by way of example and for clarity of illustration, there are assumed to be seven paths 414, although in practice there will typically be significantly more paths 414 in window 412. In some embodiments there are between approximately 10 and approximately 100 paths in the window. The processor scans spot 45 horizontally, parallel to the x-axis, from an initial x-value $x_i$ to a final x-value $x_f$, along paths 414. The scans are typically at a fixed scanning rate. Each path 414 has an effective width $y_w$ and a different y-value, processor 32 incrementing the y-values sequentially by a value $\delta y$ for each path. Typically, the value of $y_w$ is limited by the characteristics of module 22, and $y_w$ corresponds to a dimension of a pixel measured by the module. However, processor 32 is able to set the value of $\delta y$ to any convenient value, independently of $y_w$, as is described below.

Each path 414 traversed by spot 45 may be used to generate an image of the surface upon which the spot impinges, and paths 414 are also herein termed imaging paths. Where necessary, in the description herein paths 414 are differentiated by adding a suffix letter, so that the seven paths shown in FIG. 7 are separately referred to as 414A, 414B, ... 414G.

After the final x-value of a particular imaging path 414 is reached, the processor blocks charged particle beam 41 from being projected. The processor then returns the position to which spot 45 would have been focused to the initial x-value, and increments the y-value. Paths 416, also herein termed horizontal flyback paths 416, show the paths followed by the spot positions when beam 41 is blocked. Since beam 41 is blocked for the traverse of paths 416, paths 416 may not be used to form an image. Paths 416 are also termed herein non-imaging paths 416.

At the end of the lowest path 414, 414G, i.e., at the bottom right hand corner of window 412, processor 32 blocks charged particle beam 41 from being projected and returns the position to the one the spot would have been focused to, initial scanning point 1, along a vertical flyback path 418. As for paths 416, path 418 may not be used to form an image and is also termed non-imaging path 418. The complete path followed, or that would have been followed, by spot 45 within window 412 is herein termed a raster scan.

In some embodiments the time between each path 414, including the time between path 414G and 414A, is a constant $\Delta t$. However, processor 32 controls the timing between the paths, and there is no necessity that there is a constant time between them. For example, processor 32 may set the time for vertical flyback path 418 to be different from the times between adjacent paths 414.

The overall period T of the raster scan is divided into two periods, an imaging period and a non-imaging period. The imaging period corresponds to the time taken to scan from the beginning of the first imaging path, 414A, to the end of the last imaging path, 414G, and this period is also termed an imaging phase of the raster scan. The non-imaging period corresponds to the time taken to traverse the vertical flyback path 418, i.e., from the end of the last imaging path to the beginning of the first imaging path. The non-imaging period is also termed a vertical flyback phase.

Consideration of FIG. 7 shows that, neglecting end effects, a relation between a height of the raster scan, i.e., an overall y-dimension $Y_{window}$ of window 412, and $\delta y$ is given by:

$$Y_{window} = N \cdot \delta y \tag{5}$$

where N is the number of imaging paths 414.

A typical value for $Y_{window}$, the height of the raster scan, is 1 μm, and a typical value for $(x_f - x_i)$, the width of the scan, is 200 μm.

Figure 8:
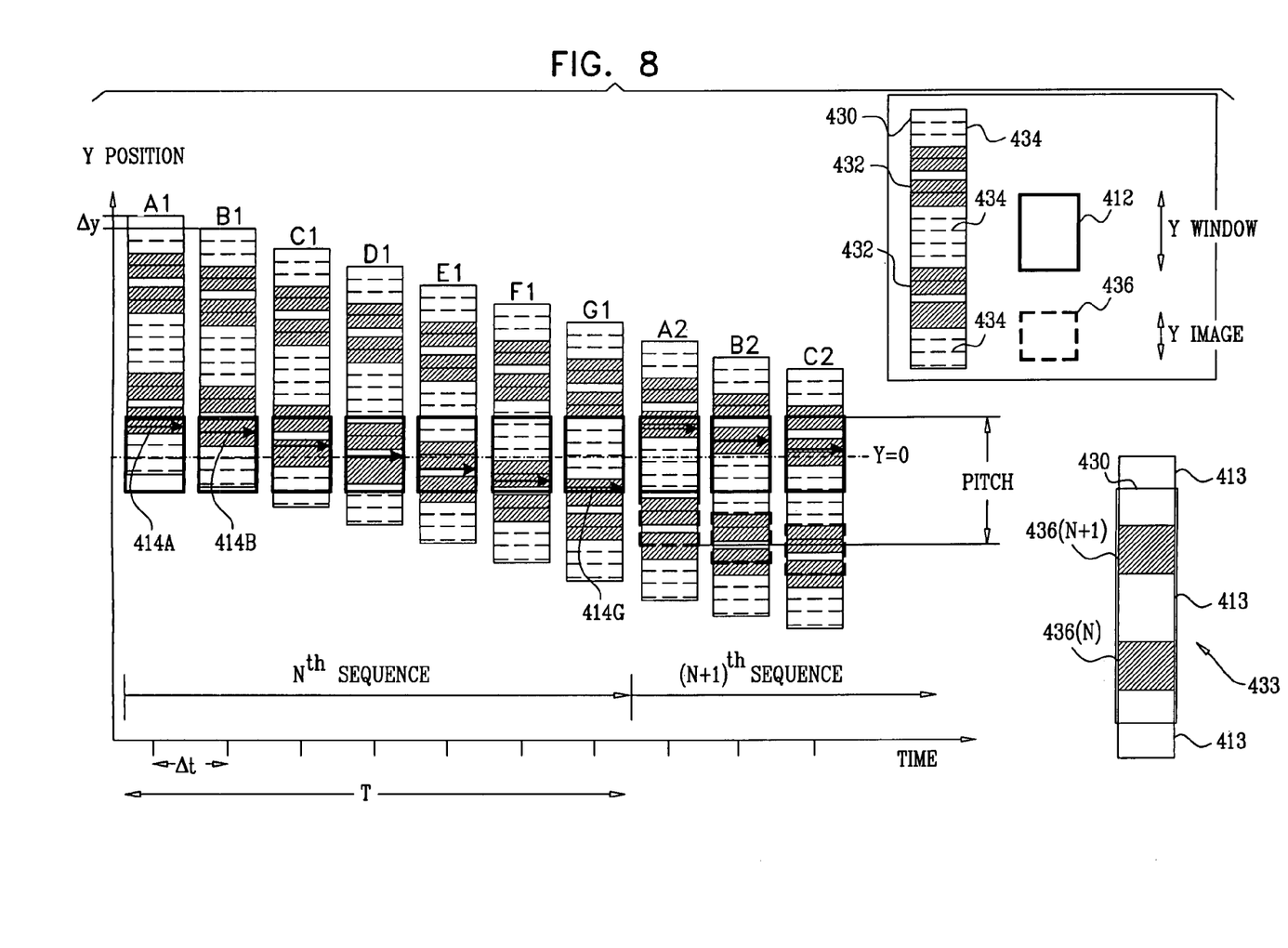
FIG. 8 is a schematic diagram illustrating a method for imaging a wafer, according to an embodiment of the present invention.

FIG. 8 is a schematic diagram illustrating a method for imaging a wafer, according to an embodiment of the present invention. The method comprises scanning spot 45 in window 412, in the raster scan described above with reference to FIG. 7, while translating the wafer relative to the window. The translation is performed with stage 36. As is described in more detail below, the combination of the raster scan of spot 45 and the translation of the wafer relative to the window allows an operator of apparatus 410 to image regions of high interest at a high resolution, while completely skipping, i.e., not imaging at all, low interest regions between the high interest regions.

In the description of the operation of apparatus 10 with reference to FIG. 5 above, it was assumed that high interest regions of wafer surface 38 were continuous conductor lines and that between the high interest regions were low interest regions. It was further assumed that the lines were aligned parallel to the y-axis, and that stage 36 translated the wafer in the y-direction. The following description of the operation of apparatus 410 assumes the same general layout of the wafer as was used with reference to FIG. 5. However, the continuous conductor lines are herein assumed to be aligned parallel to the x-axis, although stage 36 translates the wafer, as for apparatus 10, in the y-direction. Thus in apparatus 410 the alignment of the characteristic direction of the conductor lines is set to be non-parallel to, and typically orthogonal to, the translation direction.

FIG. 8 shows a series of "snapshots" A1, B1, ... C2 of a section 430 of surface 38, as time changes. Section 430 is part of a column of surface 38 that is parallel to the y-axis, and the section, also referred to herein as column 430, is assumed to have two high interest areas 432, and three low interest areas 434. Areas 432 and 434 are typically regions of the surface that continue in the x-direction on either side of section 430, so that areas 432 are typically part of a metal line conductor aligned parallel to the x-axis.

In all the snapshots, window 412 is fixed in position relative to axis 48, upon which the window is centered, as shown in FIGS. 6 and 7. The line y=0 corresponds to the position of axis 48. The different snapshots are shown assuming that stage 36 translates wafer 39 in the negative y-direction at a constant y-velocity, so that there is a fixed displacement of Δy and a fixed time of Δt between sequential snapshots.

The snapshots are assumed to be grouped in sequences, each sequence comprising a complete raster scan. The overall period T, for a complete raster scan, is also shown in FIG. 8. In a first snapshot A1 of an $N^{th}$ sequence, processor 32 aligns a top part of window 412 with a lower part of a high interest region 432, and the raster scan described above with respect to FIG. 7 is assumed to begin. Snapshot A1 shows a first imaging path 414A.

In a second snapshot B1, which occurs a time Δt after snapshot A1, stage 36 has translated wafer 39 by Δy, and the second imaging path 414B occurs. As described above with reference to FIG. 7, imaging path 414B is displaced from path 414A by δy. Succeeding snapshots C1, D1, E1, F1, and G1, are each separated by time Δt, and wafer 39 is translated by Δy. For each of the succeeding snapshots, respective imaging paths 414C, 414D, 414E, 414F, and 414G occur. Each imaging path is displaced by δy.

Processor 32 sets the displacements δy and Δy to be different. In the example described herein, the following expression holds:

$$|\delta y| < |\Delta y| \qquad (6)$$

Inspection of FIG. 8 shows that application of expression (6) results in a retrograde motion of sequential scans with respect to surface 38. As surface 38 moves down in the y-direction, imaging path scans 414 also move down in the y-direction but by smaller amounts, the result being that the scans move up the surface.

The difference in displacements given by expression (6) means that over the course of a complete raster scan, a region of surface 38 is scanned that has a y dimension Y given by:

$$Y = f(y_w, \delta y, \Delta y) \qquad (7)$$

where f is a function.

It will be understood that in the general case, a complete raster scan may have overlaps between sequential paths 414, or gaps between the paths, depending on the values of $y_w$, δy, and Δy.

In one embodiment, processor 32 sets the following condition on $y_w$, δy, and Δy:

$$|\Delta y| - |\delta y| = y_w \qquad (8)$$

The condition of expression (8) means that there are no gaps or overlaps of spot 45 on surface 38 during a complete raster scan.

In this case, assuming that there are N imaging paths 414 in a complete raster scan, the y-dimension, $Y_{image}$ of the region of surface 28 that is imaged is given by:

$$Y_{image} = N \cdot y_w \qquad (9)$$

Since typically $y_w < \delta y$, from expressions (5) and (9), $Y_{image} < Y_{window}$.

The complete raster scan of the $N^{th}$ sequence finishes at snapshot G1, after which snapshot A2 begins a new raster scan of the $(N+1)^{th}$ sequence. The region of surface 38 that has been scanned in the sequence of snapshots A1, B1, ... G1 is shown as a rectangle 436. As shown in FIG. 8, rectangle 436 progresses in the negative y-direction as stage 36 continues to move wafer in this direction. Also as apparent from FIG. 8, the first scan of the $(N+1)^{th}$ sequence, which begins with snapshot A2, is separated spatially from the last scan of the $N^{th}$ sequence, snapshot G1, by $Y_{window}$.

A diagram 433 shows imaged and non-imaged sections of column 430, after completion of the $(N+1)^{th}$ sequence. In column 430 there is a first imaged section 436(N), defined by rectangle 436 and corresponding to snapshots A1, ... G1, and a second imaged section 436(N+1). The imaged sections are preceded, separated, and followed, by sections 413 which are not imaged. The iterative process, illustrated by diagram 433, the complete set of snapshots for the first raster scan, and the partial set of snapshots for the second raster scan, continues as column 430 continues to be scanned. Imaged sections 436 (N), 436(N+1), . . . , are herein also referred to as imaged sections 436i. Although not shown for clarity in diagram 433, imaged sections 436i include areas 432, and non-imaged sections 413 include areas 434.

Non-imaged sections 413 have a y-dimension of $Y_{window}$, given by expression (5), since the y-dimension of the non-imaged sections is defined by the y-dimension of window 412. Imaged sections 436i have a y-dimension $Y_{image}$ given by expression (9). Thus, from these expressions and applying expression (8) a ratio of the heights of the imaged sections to the non-imaged sections is given by:

$$\frac{Y_{image}}{Y_{window}} = \frac{Ny_w}{N\delta y} = \frac{y_w}{\delta y} = \frac{\Delta y - \delta y}{\delta y} = \frac{\Delta y}{\delta y} - 1 \qquad (10)$$

The pitch P of the motion, i.e., the y-value for one complete imaged section 436i and one complete non-imaged section 413, is given by:

$$P = Y_{window} + Y_{image} \qquad (11)$$

For one pitch P, apparatus 410 performs N imaging scans, and so, assuming that the time taken for the non-imaging motion of spot 45 is effectively zero, the time taken for the complete pitch corresponds to the overall raster scan period T that is given by:

$$T = N \cdot \Delta t \qquad (12)$$

Combining expressions (11) and (12) gives a velocity $V_r$ of stage 36 as:

$$V_r = \frac{P}{N \Delta t} = \frac{Y_{window} + Y_{image}}{N \Delta t}. \qquad (13)$$

Since for apparatus 10 (FIG. 1), assuming that the x-dimensions of the scan and the time for one x-scan are the same as for the example described here for apparatus 410, the velocity $V_s$ of stage 36 is given by:

$$V_s = \frac{\text{pixel dimension}}{\Delta t} = \frac{y_w}{\Delta t} \quad (14)$$

where $y_w$ is the pixel dimension.

The following expression may also be derived for the ratio $$\frac{y_w}{\Delta t}:$$

$$\frac{y_w}{\Delta t} = \frac{N \Box y_w}{N \Box \Delta t} = \frac{Y_{window}}{N \Box \Delta t} \quad (15)$$

Comparing expressions (13) and (15), and using expression (14), the ratio of the velocities of stage 36 in the two systems, apparatus 410 and apparatus 10, is given by:

$$\frac{V_r}{V_s} = \frac{Y_{window} + Y_{image}}{Y_{window}} \quad (16)$$

Since in expression (16) the same number of scans are performed for the numerator and for the denominator of the fractions, expression (16) corresponds to the ratio of the throughput of the two systems.

It will be appreciated that there are a number of modifications possible to the particular embodiments described above with reference to apparatus 10 and 410. For example, in the case of apparatus 410, parameters of the raster scan, such as the vertical flyback time, the imaging scan time and/or rate, the separation between imaging scans, and the horizontal flyback time may all be altered by processor 32 to adjust which regions of surface 38 are imaged, and which regions are not imaged. Such alterations, when combined with the ability of processor 32 to set different stage velocities, enable the processor to generate scans having wide variations in their "mark-space," value, i.e., the ratio of their imaging—non-imaging y-dimensions.

In the description above it has been assumed, by way of example, that wafer 39 has been set in a specific orientation. In the examples described the wafer is set so that a direction of travel of stage 36 is either parallel to, or orthogonal to, a characteristic direction of conductor lines in the wafer. There is no necessity for such specific orientation of wafer 39, and the wafer may be oriented so that the direction of travel of stage 36 is at any convenient angle, such as 45°, to a characteristic direction of an element of interest on surface 38.

Some embodiments of the present invention combine the scanning processes of apparatus 10 and 410. The description above assumes that the rate of scan of imaging paths 414 is constant. In an alternative embodiment processor 32 sets the rate of scan of the imaging paths of the raster scan to vary in a manner similar to that described above with reference to FIG. 2 or FIG. 5. In this case the regions imaged by the raster scan comprise regions of high interest and regions of low interest within sections 436i (FIG. 8), and these regions are separated from each other by sections 413 which are not imaged at all.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for imaging a surface of an object, comprising:
   scanning at least one region of the surface with a charged particle beam, wherein during a portion of the scanning, the charged particle beam is scanned in one direction along a one-dimensional beam path;
   during the scanning in the one direction along the one-dimensional beam path, changing a scan rate of the charged particle beam from a first non-zero scan rate to a second non-zero scan rate, the first scan rate being different than the second scan rate;
   detecting a secondary electron beam comprising secondary electrons generated from an interaction between the charged particle beam and the surface; and
   generating an image of the at least one region of the surface in response to the detected secondary electron beam,
   wherein during the scanning along the one-dimensional beam path, the scanning transitions from the first scan rate to the second scan rate at a point on the one-dimensional beam path, and a location of the point is based on a current transition in the secondary electron beam, the current transition measured prior to the scanning along the one-dimensional beam path.

2. The method of claim 1, wherein a first region of the surface is scanned at the first scan rate and a second of the surface is scanned at the second scan rate, and the first region is imaged at a first resolution and the second region is imaged at a second resolution.

3. The method of claim 2, wherein a preliminary scan of the at least one region of the surface is performed, and the first and second regions of the surface are selected in response to the preliminary scan.

4. The method of claim 2, wherein the first scan rate is higher than the second scan rate and the first resolution is lower than the second resolution.

5. The method of claim 4, wherein the second region of the surface is of higher interest than the first region of the surface.

6. The method of claim 1, further comprising:
   deflecting the charged particle beam along two axes over a two-dimensional area so that the charged particle beam traces a two-dimensional beam path, and simultaneously with the deflecting, translating the object in one direction at a constant velocity, thereby scanning a first region of the surface; and
   repeating the deflecting of the charged particle beam along the two axes over the two-dimensional area, as performed during the scanning of the first region, while continuing the translation of the object, thereby scanning a second region of the surface, while not scanning a third region of the surface separating the first region from the second region.

7. An apparatus for imaging a surface of an object, comprising:
   an irradiation module configured to scan at least one region of the surface with a charged particle beam, wherein (i) during a portion of the scan, the charged particle beam is scanned in one direction along a one-dimensional beam path, and (ii) during the scan in the one direction along the one-dimensional beam path, the charged particle beam is scanned at a first non-zero scan rate and a second non-zero scan rate, the first scan rate being different than the second scan rate;

a detector configured to detect a secondary electron beam comprising secondary electrons generated from an interaction between the charged particle beam and the surface; and a processor configured to form an image of the at least one region of the surface in response to the detected secondary electron beam, wherein during the scanning along the one-dimensional beam path, the irradiation module is further configured to switch from the first scan rate to the second scan rate at a point on the one-dimensional beam path, and a location of the point is based on a current transition in the secondary electron beam, the current transition measured by the processor prior to the scanning along the one-dimensional beam path.

8. The apparatus of claim 7, wherein the irradiation module is further configured to scan a first region of the surface at the first scan rate and a second region of the surface at the second scan rate, and wherein the apparatus is configured to image the first region at a first resolution and the second region at a second resolution.

9. The apparatus of claim 8, wherein the first scan rate is higher than the second scan rate and the first resolution is lower than the second resolution.

10. The apparatus of claim 9, wherein the second region of the surface is of higher interest than the first region of the surface.

11. The apparatus of claim 8, wherein the irradiation module is further configured to perform a preliminary scan of the at least one region of the surface, and the first and second regions of the surface are selected in response to the preliminary scan.

12. The apparatus of claim 7, wherein the apparatus further comprises a stage configured to support the object, and wherein the irradiation module and the stage are configured to perform the following:

deflecting, by the irradiation module, the charged particle beam along two axes over a two-dimensional area so that the charged particle beam traces a two-dimensional beam path, and simultaneously with the deflecting, translating, by the stage, the object in one direction at a constant velocity, thereby scanning a first region of the surface; and repeating, by the irradiation module, the deflecting of the charged particle beam along the two axes over the two-dimensional area, as performed during the scanning of the first region, while continuing the translation of the object by the stage, thereby scanning a second region of the surface, while not scanning a third region of the surface separating the first region from the second region.

* * * * *